(12) United States Patent  
Skaanland et al.

(10) Patent No.: US 10,034,730 B2  
(45) Date of Patent: Jul. 31, 2018

(54) FORCE SENSOR PROVIDING CONTINUOUS FEEDBACK FOR A RESONANT DRIVE TOOTHBRUSH USING A HALL SENSOR

(71) Applicant: KONINKLIJKE PHILIPS N.V., Eindhoven (NL)

(72) Inventors: Jeffrey Thomas Skaanland, Seattle, WA (US); Harold Robert Rowan, Kenmore, WA (US); Kevin Arnold Miller, Bellvue, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 382 days.

(21) Appl. No.: 14/772,077

(22) PCT Filed: Feb. 13, 2014

(86) PCT No.: PCT/IB2014/058956  
§ 371 (c)(1),  
(2) Date: Sep. 2, 2015

(87) PCT Pub. No.: WO2014/140959  
PCT Pub. Date: Sep. 18, 2014

(65) Prior Publication Data  
US 2016/0015492 A1 Jan. 21, 2016

Related U.S. Application Data

(60) Provisional application No. 61/776,361, filed on Mar. 11, 2013.

(51) Int. Cl.  
*A61C 17/22* (2006.01)  
*A61C 17/34* (2006.01)  
*A46B 15/00* (2006.01)

(52) U.S. Cl.  
CPC .......... *A61C 17/34* (2013.01); *A46B 15/0012* (2013.01); *A46B 15/0038* (2013.01);  
(Continued)

(58) Field of Classification Search  
CPC ....... A61C 17/34; A61C 17/221; A61C 17/22; A61C 17/3409; A61C 17/3445  
See application file for complete search history.

(56) References Cited

U.S. PATENT DOCUMENTS

| | | | | |
|---|---|---|---|---|
| 5,263,218 A | * | 11/1993 | Giuliani | ................. A61C 17/20 15/22.1 |
| 2003/0135940 A1 | * | 7/2003 | Lev | ........................ A61C 17/22 15/22.1 |

(Continued)

FOREIGN PATENT DOCUMENTS

| CN | 101479497 A | 7/2009 |
|---|---|---|
| JP | 0731511 A | 2/1995 |

(Continued)

*Primary Examiner* — Michael Jennings

(57) ABSTRACT

The power toothbrush includes a brushhead arm (36) and a brush element (38) at a distal end thereof. A V-spring assembly (14) converts the movement of a power drive assembly in a back-and-forth movement. A mounting member (55) at the rear end of the V-spring assembly provides a base for a magnet (56). The back end of the V-spring assembly is displaced in accordance with pressure applied to the brush member. A Hall effect sensor (58) is mounted within the changing magnetic field produced by the magnet as the rear end of the V-spring assembly is displaced due to pressure on the brushhead. A processor (65) is responsive to the output from the Hall sensor and provides an indication when the pressure exceeds a threshold value.

13 Claims, 4 Drawing Sheets

(52) U.S. Cl.
CPC ............ *A61C 17/221* (2013.01); *A61C 17/22* (2013.01); *A61C 17/3418* (2013.01); *A61C 17/3454* (2013.01); *A61C 17/3463* (2013.01)

(56) References Cited

U.S. PATENT DOCUMENTS

| | | |
|---|---|---|
| 2003/0204924 A1 | 11/2003 | Grez et al. |
| 2003/0205492 A1* | 11/2003 | Ferber .................... A61C 17/22 206/362.2 |
| 2010/0175207 A1 | 7/2010 | Kraus et al. |
| 2011/0119848 A1* | 5/2011 | Kloster .............. A61C 17/3418 15/167.1 |
| 2012/0151698 A1* | 6/2012 | Schaefer .............. A61C 17/222 15/28 |
| 2013/0000670 A1 | 1/2013 | Binner et al. |
| 2014/0199651 A1 | 7/2014 | Adachi |
| 2015/0202030 A1* | 7/2015 | Miller ................ A46B 15/0012 15/22.1 |

FOREIGN PATENT DOCUMENTS

| | | |
|---|---|---|
| JP | 07505069 A | 6/1995 |
| JP | 2005525067 A | 8/2005 |
| JP | 2008206375 A | 9/2008 |
| JP | 2009219757 A | 10/2009 |
| JP | 2009542291 A | 12/2009 |
| JP | 2010531175 A | 9/2010 |
| JP | 2011145273 A | 7/2011 |
| JP | 2011185914 A | 9/2011 |
| JP | 2012052986 A | 3/2012 |
| JP | 2013009958 A | 1/2013 |
| JP | 2013042906 A | 3/2013 |
| RU | 2004117084 A | 3/2005 |
| WO | 9315628 A1 | 8/1993 |
| WO | 2008001302 A2 | 1/2008 |
| WO | 2011058466 A1 | 5/2011 |
| WO | 2011077287 A1 | 6/2011 |
| WO | 2014033599 A1 | 3/2014 |
| WO | 2014037856 A1 | 3/2014 |
| WO | 2014097129 A1 | 6/2014 |
| WO | 2014102667 A1 | 7/2014 |

* cited by examiner

FORCE SENSOR PROVIDING CONTINUOUS FEEDBACK FOR A RESONANT DRIVE TOOTHBRUSH USING A HALL SENSOR

CROSS-REFERENCE TO PRIOR APPLICATIONS

This application is the U.S. National Phase application under 35 U.S.C. § 371 of International Application No. PCT/IB2014/058956, filed on Feb. 13, 2014, which claims the benefit of U.S. Provisional Patent Application No. 61/776361, filed on Mar. 11, 2013. These applications are hereby incorporated by reference herein.

TECHNICAL FIELD

This invention relates generally to resonant drive magnetically actuated power toothbrushes, and more specifically concerns such a toothbrush having a pressure-sensing system.

BACKGROUND OF THE INVENTION

The use of a sensing mechanism in both power and manual toothbrushes to determine the pressure applied to the bristle field portion of the toothbrush is well known, in many different specific implementations. Typically, a sensor of some kind measures the force applied to the bristles. In many cases, the sensor includes a spring, a moment arm and a switch in which the force applied to the bristle field produces an action on the spring, which in turn drives a moment arm. When the force reaches a threshold or trigger value, a switch is operated, which sends a signal to the user that the force applied has exceeded the threshold level. The user then has the opportunity to reduce the pressure to an acceptable level.

Such a system can also be used to ensure that at least a minimum amount of pressure is applied by the user to the bristle field as well. Pressure-sensing systems, however, are often difficult to implement in a typical power or manual toothbrush. Such systems can also add significantly to the overall cost of the toothbrush and often suffer from inaccuracy.

Typically, in such pressure-sensing system, there is no continuous feedback of pressure information but only an indication of when the applied pressure has reached the threshold value indicative of excessive pressure.

Hence, a compact, simple and inexpensive sensor system for a resonantly driven system for a toothbrush is desirable, particularly one which provides continuous feedback of pressure.

SUMMARY OF THE INVENTION

Accordingly, the power toothbrush, comprising: a handle portion containing a power drive assembly; a brushhead assembly, including a brushhead arm and a brush element at a distal end thereof; a V-spring assembly responsive to the power drive assembly for converting the action of the power drive assembly to a back-and-forth action of the brushhead assembly, wherein the V-spring assembly and the brushhead assembly move together about a pivot point; a mounting member positioned at the rear end of the V-spring assembly; a magnet attached to the mounting member; a Hall effect sensor mounted within the changing magnetic field produced by the magnet as the rear end of the V-spring moves, wherein the output of the Hall effect sensor changes from a no-load condition corresponding to the displacement of the rear end of the V-spring due to pressure on the brush element; and a processor responsive to the Hall sensor output and stored information to produce a signal indicative of the pressure applied to the brush member during brushing operation.

BEST MODE FOR CARRYING OUT THE INVENTION

Figure 1:
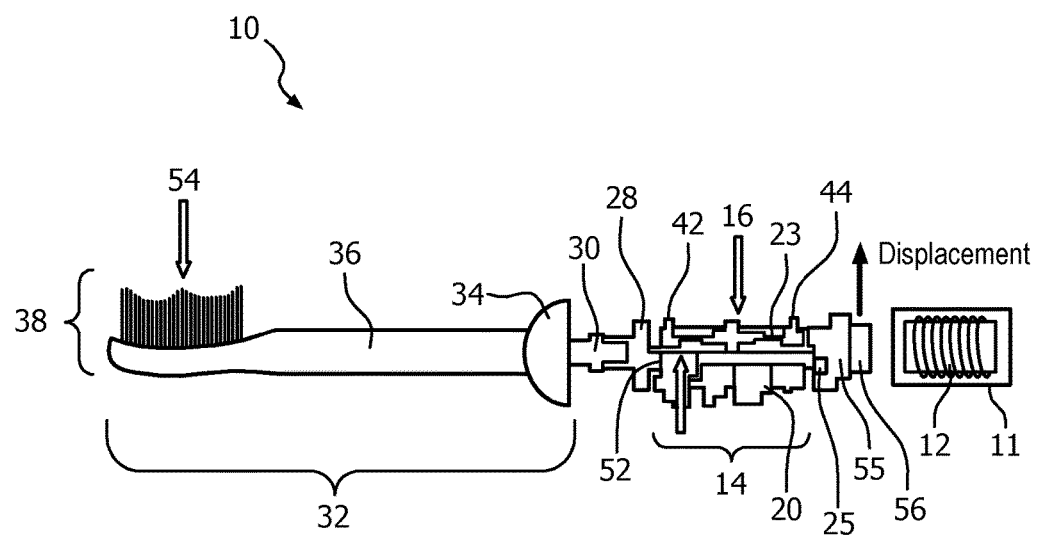
FIG. 1 is a cross-sectional view showing the major components of a power toothbrush, including the pressure-sensing system described herein.
Figure 2:
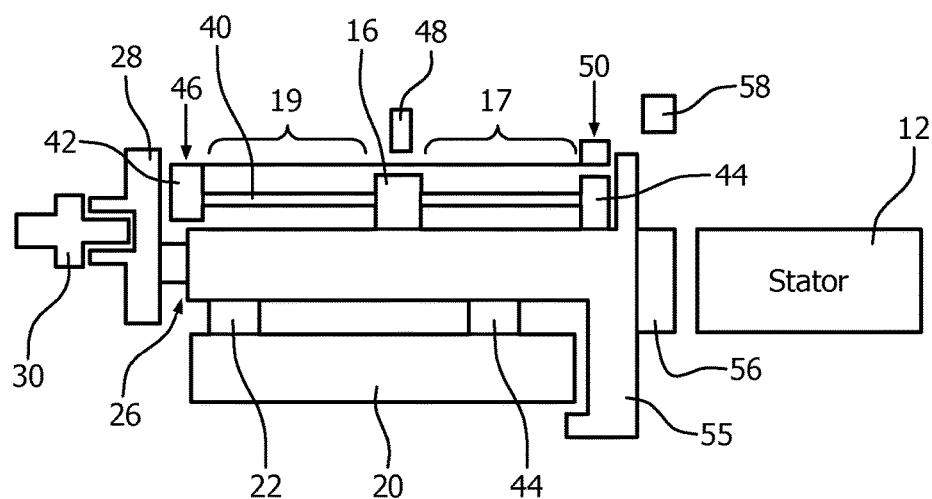
FIG. 2 is a more detailed cross-sectional view of a portion of the system of FIG. 1.

FIG. 1 shows a significant portion of a power toothbrush which includes a pressure-sensing system of the present invention. FIG. 2 shows a more detailed view of a portion of the system of FIG. 1. The power toothbrush, shown generally at 10, includes a motor (11) having a stator 12, which drives a V-spring drive assembly 14. The V-spring, shown in FIG. 2, has a center node 16 so that as a rear portion 17 of the V-spring assembly twists or rotates in one direction by action of the motor, the forward portion 19 of the V-spring assembly twists or rotates in an opposing direction. The V-spring assembly 14 is supported by a bearing block, shown generally at 20, which is in turn mounted to the housing or an internal carriage of the appliance, not shown. Extending between bearing block 20 and a lower edge of the V-spring assembly are two support bearings 22 and 24. The V-spring assembly 14 can encompass a variety of different embodiments. The forward end 26 of the V-spring assembly mates with a support member 28 from which extends a mounting blade 30. Removably positioned on mounting blade 30 is a brushhead assembly 32, which includes a proximal portion 34 which mates with the handle of the toothbrush. The brushhead assembly includes an elongated arm 36 at the distal end on which is a brush member 38 which includes a bristle field. In a typical action, the brush member will move back and forth through a specified angle, e.g. 9-11°, to accomplish cleansing of the teeth.

Referring still to FIGS. 1 and 2, adjacent the upper surface of V-spring assembly 14 is a node member 23 which extends substantially the length of the V-spring assembly. Positioned adjacent the upper surface of node member is a leaf spring 40, which also extends approximately the length of and overlays the upper portion of the V-spring assembly. The node member and the leaf spring are connected by bearing elements 42 and 44 to opposing ends of the V-spring assembly. Connected to bearings 42 and 44 and node point 16 are spring members 46, 48 and 50. Springs 46 and 50 provide a preload on the leaf spring 40.

The brushhead assembly and the V-spring assembly together pivot about a point 52 near the forward end of the V-spring assembly approximately at bearing 22, while springs 48 and 50 at node 16 and the rear bearing 44 tend to resist displacement.

As force is applied against the bristle field during brushing action (arrow 54), the brushhead assembly will tend to move, rotating about the pivot point 52. The V-spring assembly will move in the opposing direction. The force applied against the bristle field is often referred to as pressure. This force, or load, on the bristle field is primarily produced by user action, although additional load is produced by the cheeks and the lips of the user during normal brushing. It is this total load, or force, which the sensing system described below determines.

Referring still to FIGS. 1 and 2, a ferrous mounting element 55 is secured to a rear end 25 of the V-spring assembly. Positioned at the rear surface 56 of the mounting element is a magnet 56. The magnet in the embodiment shown has the following dimensions: 13.4×9.0×4.0 (mm). One example of a suitable magnet is Neodymium. Positioned away from the magnet 56, but within the magnetic field produced by the magnet, is a Hall effect sensor 58. In the embodiment shown, the Hall effect sensor is conventional and can be purchased commercially. One example of a suitable Hall effect sensor is an Austria Microsystems AS5510. In the embodiment shown, the Hall effect sensor is mounted on the drive tram frame in the toothbrush and is located approximately 2.3 mm from the magnet, approximately in the same plane thereof. Other Hall effect sensors could be used, as long as they have sufficient sensitivity to the changing magnetic field as the magnet moves back and forth, displacing laterally due to force on the bristle field.

Figure 3:
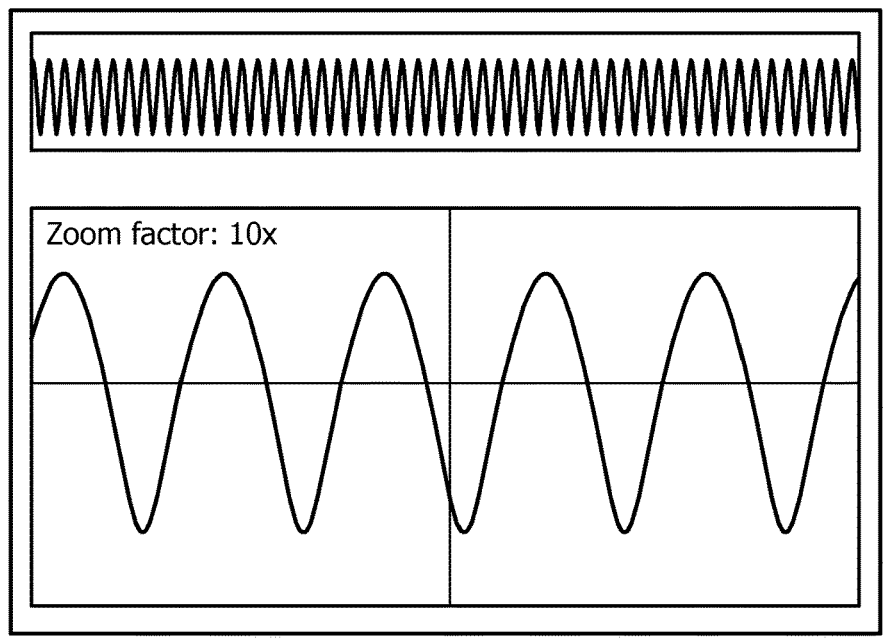
FIG. 3 is a diagram of the output of the Hall effect sensor portion of the present system.

In operation, without any force on the bristle field, as the rear end of the V-spring and the magnet swing back and forth through a selected angle, without lateral displacement, the voltage output of the Hall effect sensor varies sinusoidally, as shown in FIG. 3. Basically, the voltage output of the Hall effect sensor will vary in response to a changing magnetic field. A changing magnetic field provides a basis for determining the amount of force being applied to the bristle field. As force is applied to the bristle field, the V-spring assembly pivots, moving the rear end of the V-spring and the magnet, against the action of spring 50, producing a lateral displacement of the magnet in the direction of the Hall effect sensor. The Hall effect sensor is sensitive enough to detect change in the magnetic field as the magnet comes closer to the sensor. The toothbrush includes in its microprocessor a table of information in the form of a response curve which relates the voltage output of the Hall effect sensor to the displacement of the magnet and hence the force applied to the brush element. The displacement of the magnet will result in a change of voltage output of the Hall sensor relative to the voltage output under no-load conditions. Accordingly the change in the sensor output is a reliable indication of the force being applied to the bristle field.

Figure 6:
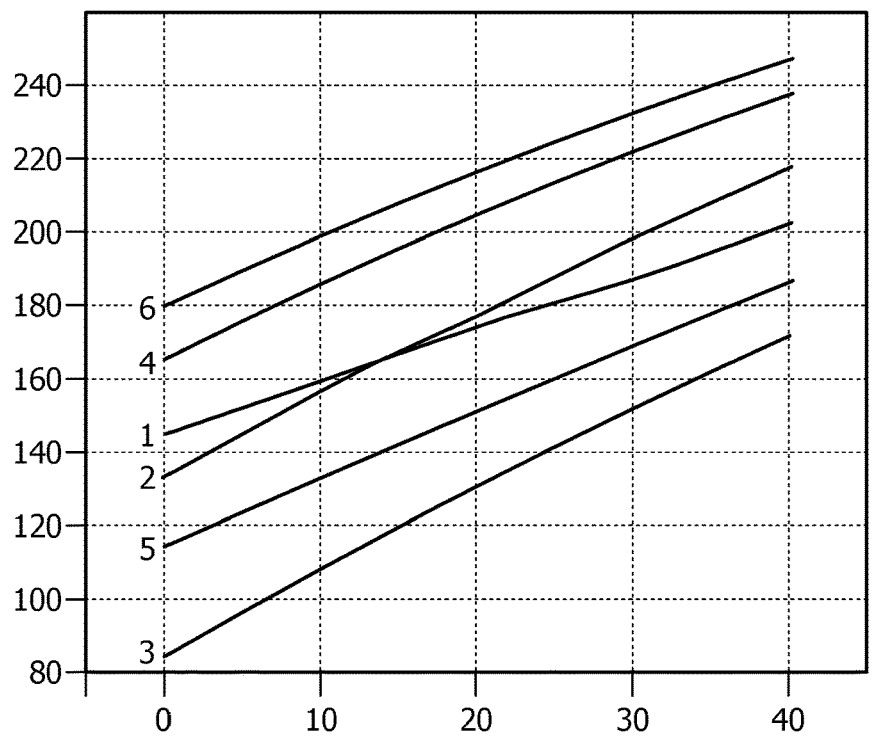
FIG. 6 is a graph showing uncompensated outputs for a specific Hall effect sensor.

In a power toothbrush as described above, the use of a Hall effect sensor to determine force/pressure is sensitive to temperature. The variations in temperature between manufacture of the toothbrush and actual use-to-use, will accordingly result in variations of the sensor function and output, which ultimately will reduce accuracy of the pressure output. The typical variation, for instance, in temperature of the Austria Microsystem AS5510 Hall effect sensor is shown in FIG. 6. This illustrates the rather significant variation in output relative to temperature for several series' of the particular sensor. Temperature sensitivity is true for other Hall effect sensors as well.

Figure 7:
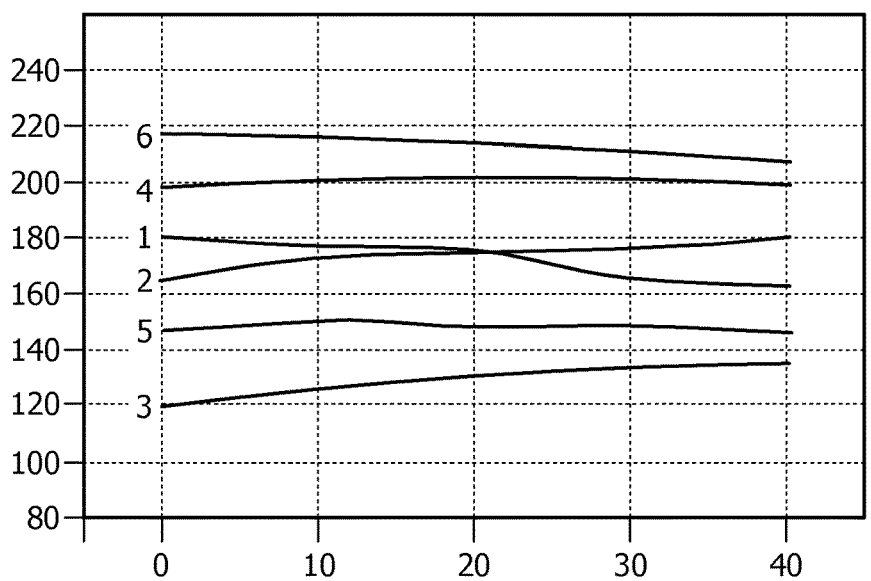
FIG. 7 is a graph showing compensated outputs for the Hall effect sensor of FIG. 6.

The temperature curves, such as shown in FIG. 6, for a particular Hall effect sensor are stored in the processor/memory in the handle of the toothbrush. The toothbrush will include a temperature sensing member 69 in the handle. The temperature sensing member could be on board the processor or a separate location within the handle. For each value of temperature, there will be stored in the processor/memory a temperature constant which adjusts the Hall effect output for that temperature, resulting in a temperature/output table. The processor will adjust the Hall effect output in accordance with the stored temperature/output table. At the lower temperatures, the output will be increased to some extent, whereas at the higher end of the temperature range, the sensor output will be decreased, resulting in a Hall effect output which is consistent over a selected range of temperatures for a particular applied pressure/force. A temperature-compensated Hall effect output is shown in FIG. 7. FIGS. 6 and 7 cover a range of temperatures between 0 and 40 degrees Celsius. This temperature compensation system results in a more accurate Hall sensor output, which in turn results in more accurate pressure information determined by the processor and fed back to the user.

Figure 4:
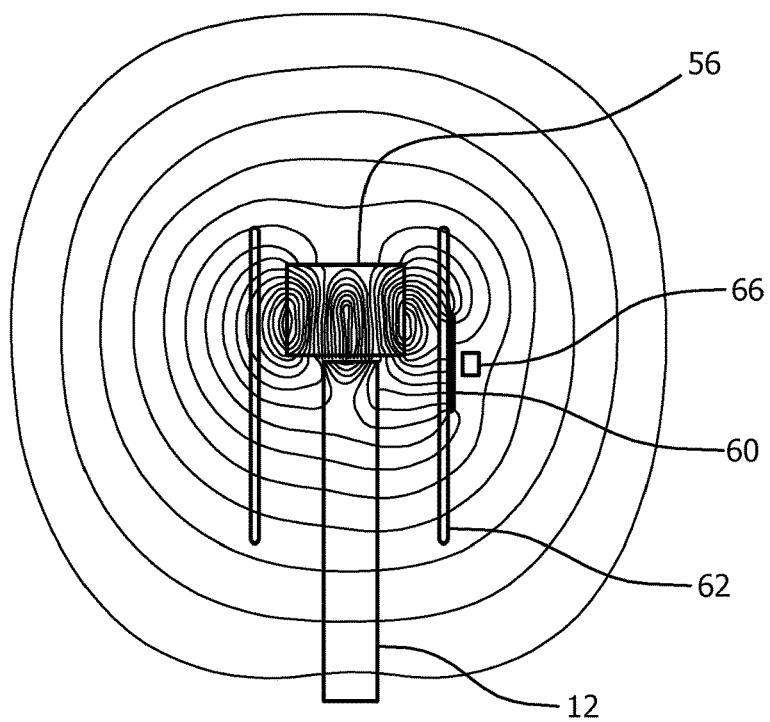
FIG. 4 is a simplified magnetic field diagram showing the structure of the pressure-sensing system of FIG. 2 with a shield.

The sensitivity of the Hall effect sensor may in some cases be too high relative to the magnetic field. Such a problem is overcome by the use of a magnetic shield member 60, shown in FIG. 4, mounted on the drive housing 62 between the magnet 56 and the Hall effect sensor 66. Various shielding arrangements can be used, but one example is the use of mu metal foil. Mild steel could also be used. In the embodiment shown, the thickness of the mu metal is approximately 0.3 mm. Such an arrangement decreases the sensitivity of the sensor so as to provide an accurate response to changes in the magnetic field as the magnet is displaced due to force in the bristle field.

Figure 5:
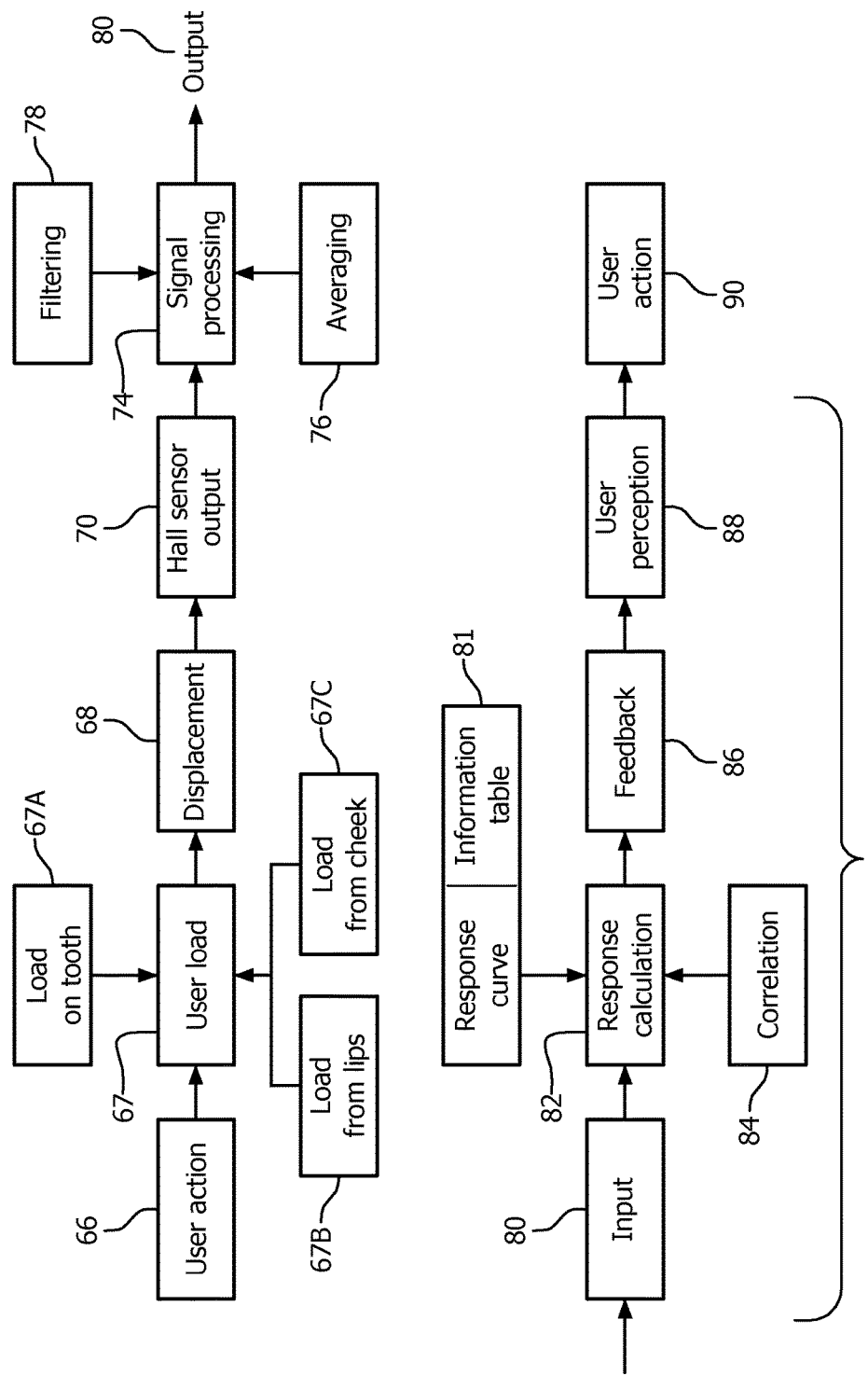
FIG. 5 is a diagram of the processing of the output signal from the Hall effect sensor shown in FIGS. 1, 2 and 4.

FIG. 5 shows the overall process and structural elements for accomplishing the force determinations, by a processor 65. The user action is represented at block 66, indicating the amount of or force applied against the bristle field. The total user load is represented at 67. User load includes the load actually applied by the user 67A, as well as load due to the user's lips 67B and the user's cheeks 67C during brushing. This results in a total load or force on the bristle field, which creates a displacement of the rear end of the V-spring and the magnet about the pivot, represented by block 68. The displacement produces a signal from the Hall sensor, as represented by block 70.

The Hall output signal is then processed at block 74, determining the change in the voltage and output due to the total load; processing includes averaging the output over a number of cycles, referred to at 76, as well as filtering noise from the signal, including electronic noise and mechanical noise from the motor, represented at 78. The result is an output signal 80 which is the input signal to the remainder of the processing circuit. As indicated above, the microprocessor includes a response curve or a table of information 81 which relates Hall sensor output to a force value. The response curve is typically a straight line for a range of 0-300 grams of force. The calculation also will include a correlation step, as represented at 84, which involves correlation of force and Hall sensor values over the force range. The output of the calculation 82 will be an indication of (1) whether a minimum pressure has been reached; (2) whether the pressure is within a preselected range and (3) whether a maximum pressure value has been exceeded. The information is provided continuously. As an example, a minimum pressure could be 30 grams, while a maximum pressure could be 300 grams.

This information is proved as feedback (block 86) in some form, e.g. auditory, visual or sensory. This feedback is perceivable by the user, as shown at 88, which enables the user to take appropriate action, specifically to increase or decrease the pressure or maintain the present pressure if the pressure is within the desired range, as generally represented by block 90. One indication that a maximum pressure has been exceeded (a trigger point) is by changing the frequency slightly, usually 10 Hz or so, higher, for a short period of time, e.g. two seconds, and then reverting back to the established frequency thereafter. This perceptible feedback and the user's reliance on it to make changes in brushing habits is desirable to produce long-range good dental care.

It should be recognized that a simple, reliable system for providing pressure information on the brushhead is disclosed herein, the system provides continuous information on pressure against the brush field.

Although a preferred embodiment of the invention has been disclosed for purposes of illustration, it should be understood that various changes, modifications and substitutions may be incorporated in the embodiment without departing from the spirit of the invention, which is defined by the claims which follow.

What is claimed is:

1. A power toothbrush, comprising:
    a handle portion containing a power drive assembly;
    a brushhead assembly, including a brushhead arm and a brush element at a distal end thereof;
    a V-spring assembly responsive to the power drive assembly for converting the action of the power drive assembly to a back-and-forth action of the brushhead assembly, wherein the V-spring assembly and the brushhead assembly move together about a pivot point;
    a mounting blade extending from a forward end of the V-spring assembly which is removably connected to the brushhead assembly that drives the brush element when the V-spring assembly and brushhead assembly move about the pivot point;
    a mounting member positioned at the rear end of the V-spring assembly;
    a magnet attached to the mounting member;
    a Hall effect sensor mounted within changing magnetic field produced by the magnet as the rear end of the V-spring moves, wherein the output of the Hall effect sensor changes from a no-load condition corresponding to the displacement of the rear end of the V-spring due to pressure on the brush element; and
    a processor responsive to the Hall sensor output and stored information to produce a signal indicative of the pressure applied to the brush member during brushing operation.

2. The power toothbrush of claim 1, wherein the power drive assembly includes a motor having a stator portion which drives the V-spring assembly.

3. The power toothbrush of claim 1, wherein the mounting member comprises a ferrous metal.

4. The power toothbrush of claim 1, wherein the V-spring assembly has a node point approximately midway along the length thereof, wherein when a rear portion of the V-spring twists in one direction by action of the power drive assembly, a forward portion of the V-spring twists in the opposing direction, producing a back-and-forth sweeping action of the brushing assembly and the brush member.

5. The power toothbrush of claim 1, including a spring assembly which provides a preload at opposing ends of the V-spring assembly.

6. The power toothbrush of claim 1, including a metal shield positioned between the magnet and the Hall effect sensor to reduce the sensitivity of the Hall effect sensor to the changing magnetic field generated by the magnet, as the magnet is displaced by pressure on the brush member.

7. The power toothbrush of claim 1, wherein the processor includes a capability of averaging the signal output of the Hall sensor over several cycles and for filtering out noise from the Hall signal output.

8. The power toothbrush of claim 1, wherein the processor uses the stored information to correlate the output of the Hall sensor with at least one pre-established threshold and to provide a feedback information to the user relative to the pressure on the brush member exceeding a first threshold value.

9. The power toothbrush of claim 8, wherein the processor provides an indication to the user relative to pressure on the brush member exceeding a minimum threshold.

10. The power toothbrush of claim 9, wherein the indication is in a form recognizable by the user.

11. The power toothbrush of claim 1, wherein the signal produced by the processor is continuous providing a continuous indication of pressure on the brush member.

12. The power toothbrush of claim 1, including a system for temperature compensation of the Hall effect sensor output.

13. The power toothbrush of claim 12, including a temperature-determining element and a stored code or table relating a sensed temperature to an adjustment of the Hall effect sensor output, such that the output of the Hall effect sensor for a given pressure will remain approximately constant over a selected range of temperature.

* * * * *